(12) United States Patent
Piantoni et al.

(10) Patent No.: US 8,640,756 B2
(45) Date of Patent: Feb. 4, 2014

(54) MACHINE FOR MANUFACTURING PERSONAL SANITARY ITEMS

(75) Inventors: Matteo Piantoni, Albino (IT); Federica Alberti, Crema (IT)

(73) Assignee: GDM S.p.A. (IT)

( * ) Notice: Subject to any disclaimer, the term of this patent is extended or adjusted under 35 U.S.C. 154(b) by 0 days.

(21) Appl. No.: 13/139,181

(22) PCT Filed: Mar. 5, 2010

(86) PCT No.: PCT/IB2010/050959
§ 371 (c)(1),
(2), (4) Date: Jun. 10, 2011

(87) PCT Pub. No.: WO2010/103444
PCT Pub. Date: Sep. 16, 2010

(65) Prior Publication Data
US 2011/0245058 A1    Oct. 6, 2011

(30) Foreign Application Priority Data
Mar. 9, 2009    (IT) ............................. BO2009A0139

(51) Int. Cl.
*B29C 65/00*    (2006.01)
*B32B 37/00*    (2006.01)
*B32B 38/04*    (2006.01)
*B32B 38/10*    (2006.01)

(52) U.S. Cl.
USPC ............ 156/512; 156/519; 156/522; 156/552

(58) Field of Classification Search
USPC ......... 156/519, 265, 270, 552, 301, 302, 512, 156/522
See application file for complete search history.

(56) References Cited

U.S. PATENT DOCUMENTS

| | | | |
|---|---|---|---|
| 4,735,673 A | 4/1988 | Piron | |
| 6,059,710 A | 5/2000 | Rajala | |
| 6,242,074 B1 | 6/2001 | Thomas | |
| 6,248,202 B1 * | 6/2001 | Corzani et al. | 156/270 |
| 6,527,902 B1 | 3/2003 | Rajala | |

FOREIGN PATENT DOCUMENTS

| | | |
|---|---|---|
| DE | 19805335 | 8/1999 |
| WO | 01/05622 | 8/2001 |

OTHER PUBLICATIONS

International Search Report dated Jun. 10, 2010 from counterpart application.

* cited by examiner

*Primary Examiner* — Linda L. Gray
(74) *Attorney, Agent, or Firm* — Timothy J. Klima; Shuttleworth & Ingersoll, PLC

(57) ABSTRACT

Personal sanitary items are manufactured by a machine comprising a first feed system (2) directing a first continuous web (3) of material along a given feed path (P), a device (9) serving to make a succession of absorbent pads and apply the single pads to the first web (3) of material, and a second feed system (19) supplying a second continuous web (20) of material that is bonded ultimately to the first web (3), with the pads sandwiched between, to produce a continuous succession of sanitary items. The pad-making device (9) comprises at least one cutter (12) by which a continuous band (11) of absorbent material is divided up to produce the succession of pads, and the feed path (P) follows a convoluted trajectory substantially of "S" configuration.

12 Claims, 2 Drawing Sheets

MACHINE FOR MANUFACTURING PERSONAL SANITARY ITEMS

This application is the National Phase of International Application PCT/IB2010/050959filed Mar. 5, 2010 which designated the U.S. and that International Application was published under PCT Article 21(2) in English.

This application claims priority to Italian Patent Application No. BO2009A000139filed Mar. 9, 2009 and PCT Application No. PCT/IB2010/050959 filed Mar. 5, 2010, which applications are incorporated by reference herein.

TECHNICAL FIELD

The present invention relates to a machine for manufacturing personal sanitary items.

The invention finds application, to advantage, in the manufacture of personal sanitary products such as nappies (diapers) for babies, sanitary napkins for women, incontinence pads and the like.

BACKGROUND ART

Conventional machines for the manufacture of personal sanitary products comprise feed means supplying a first continuous web of material, and a device serving to fashion a succession of absorbent pads that are then placed on the first web, the surface of the web having been primed with adhesive. The first web, providing the so-called backsheet, is made typically of an impermeable plastic material such as PET, for example.

The pads are fashioned by a device that comprises feed means supplying a band of cellulose, and grinding components by which the cellulose is broken up to produce an incoherent mass of fibres, or fluff.

The fibres are then gathered into special vacuum pockets to form the pads, ready for application to the first web.

The first web of material is carried by a conveyor and directed along a rectilinear feed path. By way of example, the rectilinear conveyor consists in a transport belt.

The pads are applied to the first web at a given point along the rectilinear feed path. Thereafter, likewise along the rectilinear path, other discrete parts are fashioned and applied to the items in production by dedicated auxiliary systems.

In the case of a baby's nappy (diaper) or an adult incontinence pad, for example, a succession of front and rear panels may be added to provide closure tabs.

Thus, in prior art machines for manufacturing personal sanitary items, all the assembly steps take place along the rectilinear path.

Prior art machines also comprise feed means supplying a second web of material that is bonded to the first web in such a way that the pads, at least, remain sandwiched between the two webs.

The second web, providing the so-called topsheet, is made of a nonwoven fabric and constitutes the part of the product placed in direct contact with the wearer.

The continuous web of assembled materials is divided at a cutting station into a succession of discrete items.

Disadvantageously, machines of the prior art are affected by certain drawbacks.

Firstly, the use of pads consisting in a mass of incoherent fibres dictates that space must be dedicated specifically to a line for the preparation of such a material. Consequently, the overall dimensions of conventional machines are decidedly large.

Moreover, since the pads are fashioned from incoherent material that is highly volatile and liable to scatter, they must be handled with appreciable care and delicacy, even after being applied to the first web.

Accordingly, the number of defective items produced is by no means negligible, given that the handling of the first web along the rectilinear path is not always precise. In particular, the first web frequently becomes misaligned, so that the pads and/or other additional components will be positioned incorrectly when placed on the web, and the defective item must be discarded.

DISCLOSURE OF THE INVENTION

Accordingly, the object of the present invention is to provide a machine for manufacturing personal sanitary items, wherein the drawbacks associated with the prior art as described above are overcome.

One object of the present invention, in particular, is to provide a machine of notably compact dimensions for manufacturing personal sanitary items.

A further object of the invention is to provide a machine for manufacturing personal sanitary items wherein the number of defective items rejected during production is significantly reduced.

The stated objects of the present invention are substantially realized in a machine for manufacturing personal sanitary items, of which the characteristics are as recited in one or more of the appended claims.

BRIEF DESCRIPTION OF THE DRAWINGS

The invention will now be described in detail, by way of example, with the aid of the accompanying drawings, in which.

DETAILED DESCRIPTION OF THE PREFERRED EMBODIMENTS OF THE INVENTION

Figure 1:
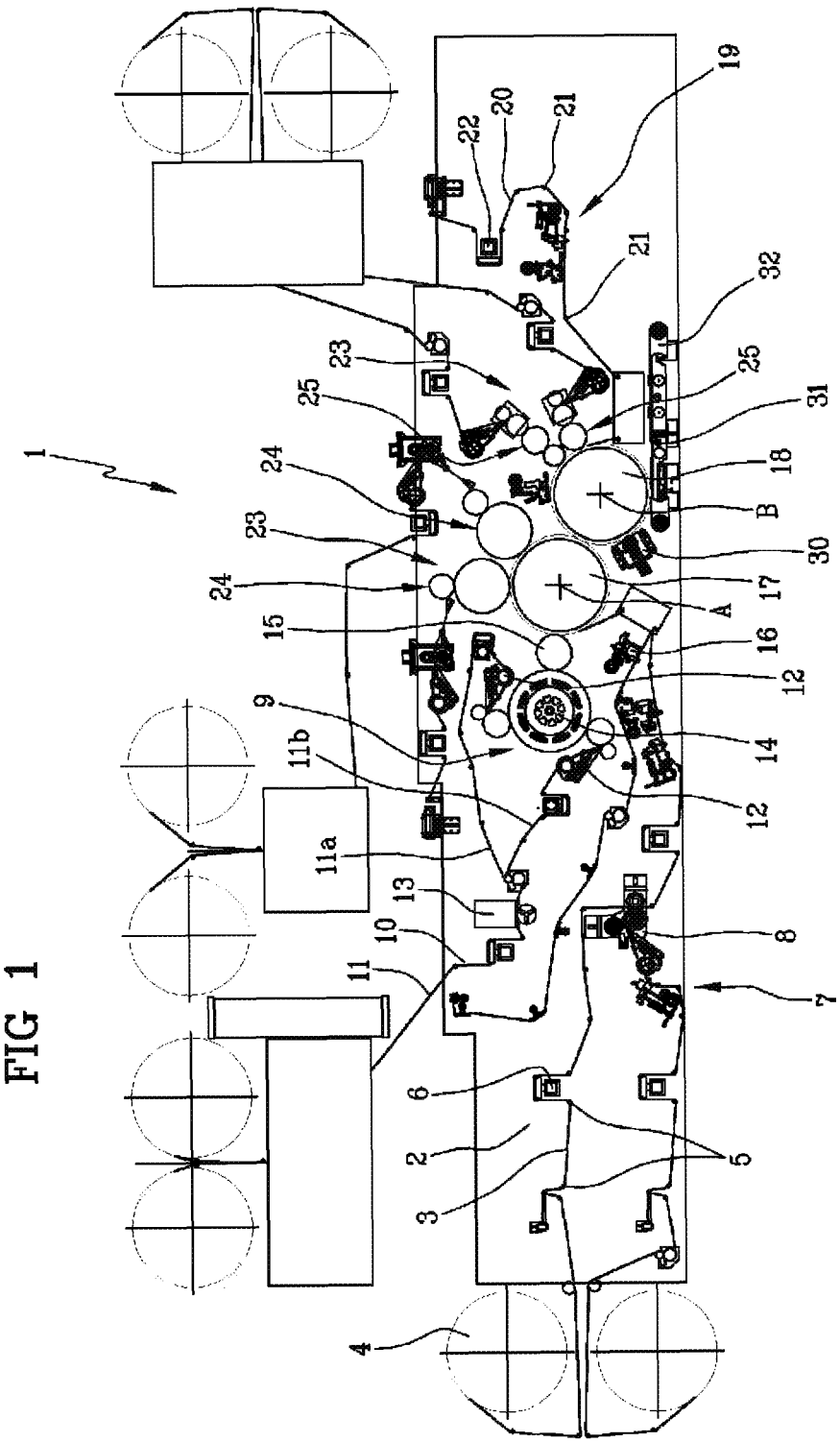
FIG. 1 shows a machine for manufacturing personal sanitary items according to the present invention, illustrated in a schematic side elevation view.

With reference to the accompanying drawings, numeral 1 denotes a machine for manufacturing personal sanitary items, in its entirety, according to the present invention.

The machine 1 in question comprises first feed means 2 supplying a first continuous web 3 of material, wound initially on a respective roll 4. The first web 3 is made preferably of an impermeable plastic material, such as polyethylene terephthalate (PET), and provides what is known generally as a backsheet.

The first feed means 2 comprise a plurality of idler and tensioning rollers, denoted 5, and at least one alignment system 6 by which the first web 3 is guided and maintained at the correct tension.

In the embodiment described and illustrated, the first feed means 2 also comprise an auxiliary device 7 by which an additional component is prepared and applied to the first web 3.

The auxiliary device 7 comprises a cutting and placing mechanism 8 by which additional components are cut to size and associated in succession with the first web 3.

By way purely of example, the additional component could be a strip of plastic material attached externally to the sanitary item, to which discrete accessory elements are attachable subsequently, as will become clear in due course.

The machine 1 further comprises a device 9 serving to prepare a succession of absorbent pads for personal sanitary items. The pads made by the device 9 are also applied to the first web 3 by this same device.

The pad-making device 9 comprises feed means 10 supplying a continuous band 11 of absorbent material, already formed and stable, and at least one cutter mechanism 12 by which the band 11 of absorbent material is divided into a succession of single pads.

In the example illustrated, the pad-making device 9 comprises cutting means 13 located upstream of the cutter mechanism 12, allowing the band 11 of absorbent material to be divided into two distinct portions 11a and 11b.

More precisely, the pad-making device 9 is equipped with two cutter mechanisms 12 by which the portions 11a and 11b are cut from the band 11 to create two respective portions of padding.

The two portions are positioned on a formation wheel 14, staggered one relative to another and providing pads contoured to a selected shape.

The pad-making device 9 also comprises a transfer mechanism 15 by which the single pads are taken up from the formation wheel 14 and placed on the first web 3.

In the example illustrated, the formation wheel 14 and/or the transfer mechanism 15 are preferably vacuum components.

The machine 1 further comprises a dispenser 16 of adhesive positioned upstream of the pad-making device 9 and operating on the first web 3. The dispenser 16 is designed to prime the first web 3 with a quantity of adhesive such as will ensure that the pads, at least, will be applied stably to the selfsame first web 3.

Figure 2:
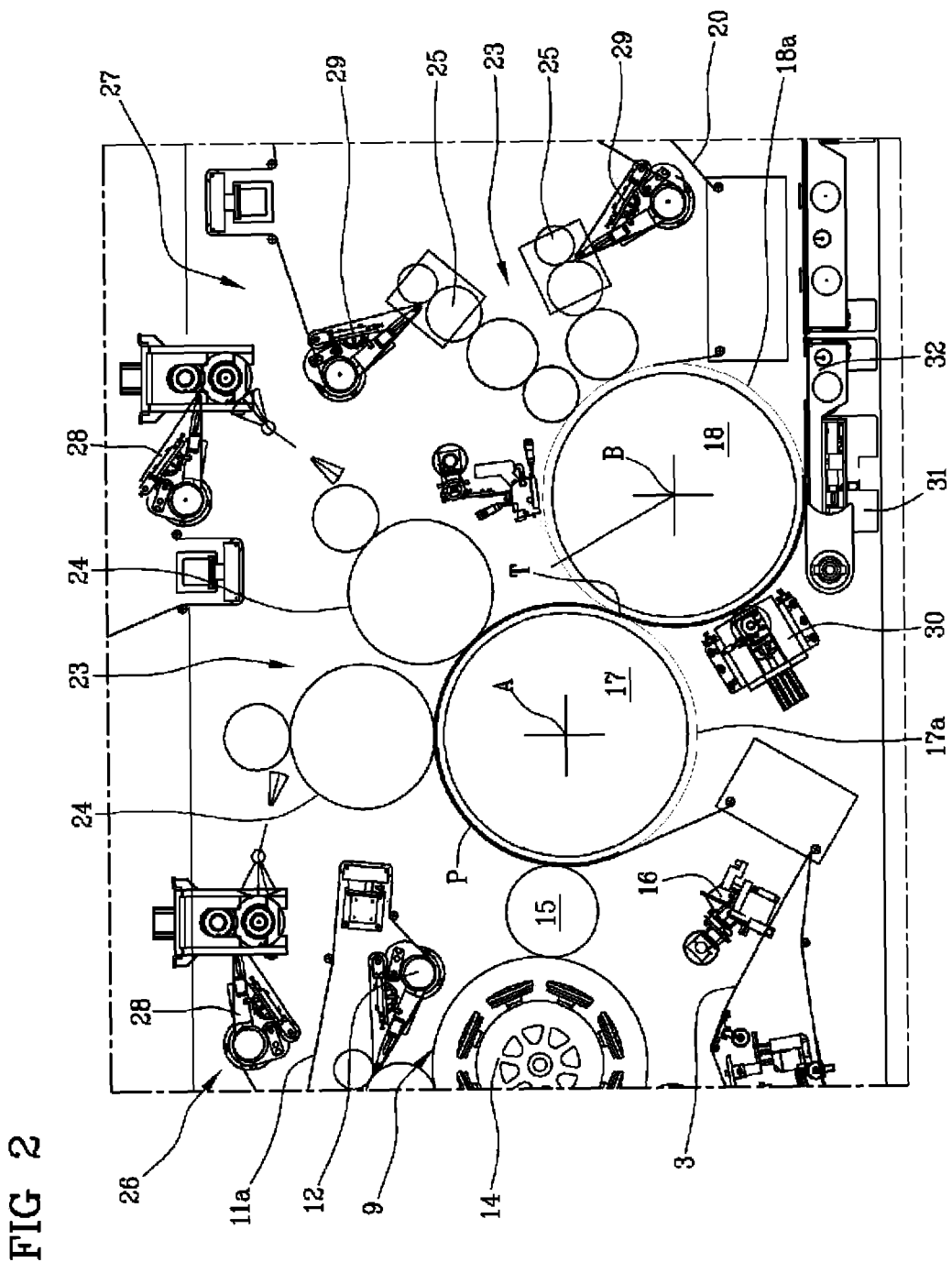
FIG. 2 shows a portion of the machine in FIG. 1, illustrated in a schematic side elevation view.

To advantage, using a previously prepared and stable absorbent material, the first web 3 can be directed along a feed path "P" describing a convoluted trajectory substantially of "S" configuration, thus reducing the space needed to assemble the personal sanitary items (FIG. 2).

To this end, the machine 1 comprises a first roller 17, and a second roller 18 paired with the first, around which the first web 3 is wrapped and fed continuously.

The first and second rollers 17 and 18 rotate in opposite directions and tangential one to another, thereby combining to establish the feed path "P" of "S" configuration.

The first roller 17 is associated with the pad-making device 9 and positioned downstream of this same device.

More exactly, the transfer mechanism 15 of the pad-making device 9 is placed substantially tangential to the first roller 17, in such a way that the completed pads can be transferred from the formation wheel 14 onto the first web 3 at a point coinciding with the first roller 17.

Consequently, the adhesive dispenser 16 occupies a position upstream of the first roller 17.

The first roller 17 and the second roller 18 turn on respective axes of rotation denoted A and B which, in the embodiment illustrated, are placed at different heights.

More precisely, the axis of rotation A of the first roller 17 is positioned at a level higher than the axis of rotation B of the second roller 18.

With the axes of rotation A and B arranged in this way, the machine 1 is rendered still more compact.

Advantageously, the operating surfaces 17a and 18a presented by the first roller 17 and the second roller 18, respectively, are rubber-coated. In other words, the operating surfaces 17a and 18a are covered with a layer of rubber material (not illustrated in the drawings), so that friction generated between the first web 3 and the two surfaces 17a and 18a will ensure that the web clings firmly to the first and second rollers 17 and 18. This in turn ensures the first web 3 can be guided with precision during its progress.

Likewise in order to enable precise handling of the first web 3, both the first roller 17 and the second roller 18 will preferably present aspirating surfaces.

In other words, the machine 1 comprises vacuum means (not illustrated) such as will generate an aspirating flow of air through a plurality of holes (not illustrated) in the operating surfaces 17a and 18a of the rollers 17 and 18.

The machine 1 further comprises second feed means 19 supplying a second continuous web 20 of material wound initially on a respective roll (not illustrated in the drawings). The second web 20 is bonded to the first web 3 at least after the pads have been applied to the first web 3. Accordingly, the pads remain sandwiched between the first web 3 and the second web 20.

The second web 20 consists preferably of nonwoven fabric and provides what is known generally as a topsheet. The material of the second web 20 is that placed in direct contact with the body of the wearer.

The second feed means 19 comprise a plurality of idler and tensioning rollers, denoted 21, and at least one alignment system 22 by which the second strip 3 is guided and maintained at the correct tension.

The second feed means 19 are associated with the second roller 18. Thus, the second web 20 is supplied to the second roller 18 in such a way that it can be paired with the first web 3 advancing from the first roller 17, together with the pads, at a point of tangency T between the first roller 17 and the second roller 18.

The assembled components of the product are compressed between the rollers 17 ad 18 at the point of tangency T, so as to improve the bond between the first web 3 and the second web 20.

Thus, the assembled sanitary items emerge from the rollers 17 and 18 in a continuous succession, joined one to the next.

In the example illustrated, the machine 1 further comprises means 23 by which discrete accessory elements are prepared and applied to the personal sanitary items.

As discernible from the drawings, such means 23 for preparing and applying discrete accessory elements operate both on the first web 3 and on the second web 20.

To this end, the means 23 in question occupy positions adjacent both to the first roller 17 and to the second roller 18.

In the example illustrated, means 23 for preparing and applying discrete accessory elements comprise a pair of first devices 24 associated with the first roller 17 and a pair of second devices 25 associated with the second roller 18.

Both the first devices 24 and the second devices 25 comprise respective feed means 26 and 27 supplying a strip material, and respective cutting mechanisms 28 and 29 by which the discrete elements are severed from the strip.

By way of example, the first devices 24 produce a succession of front panels and a succession of rear panels, respectively, associated with the first web 3 and needed for the purpose of fastening the sanitary item when in use.

The second devices 25 are designed to apply further elements to the second web 20, before this same second web is bonded to the first web 3.

The machine 1 also comprises a sealing roller 30, operating by compression, located adjacent to the second roller 18 at a point downstream of the point of tangency T.

Numeral 31 denotes an outfeed conveyor 31 to which the aforementioned continuous succession of sanitary items is released. The conveyor 31 is positioned adjacent to the second roller 18, immediately downstream of the sealing roller 30. In the example illustrated, the outfeed conveyor 31 comprises a rectilinear transport belt 32.

Further along the conveyor 31, the continuous succession of assembled items will be divided into discrete units by a cutter device (not illustrated).

The stated objects are achieved by the invention, which affords significant advantages.

In effect, with the absorbent pads made from a previously prepared and stable fluff material, the machine no longer requires a dedicated line serving to process the fluff from a starting material. Consequently, the overall dimensions of the machine are reduced significantly.

In addition, the absorbent material can be managed more practically, more easily and more quickly. Accordingly, the web of backsheet material can be routed along a convoluted path of "S" configuration as described and illustrated, reducing the length of the machine still further without any adverse effect on the items in production.

Moreover, with the convoluted path of "S" configuration established by the rollers, the first web can be kept in the correct position much more easily.

This means in turn that items can be assembled more quickly, but more especially with greater precision and fewer production rejects.

To advantage, lastly, a reduction in the overall length of the machine has the effect also of reducing the distance between the point at which adhesive is applied and the point at which the assembly of the items is completed. Accordingly, rejects attributable to possible machine stoppages are similarly reduced. In practice, should the operation of the machine be interrupted, rejects would be limited to the unfinished items situated between the point at which the adhesive is applied and the point at which assembly is completed, that is to say, items to which adhesive had been applied and then lost its tackiness before the assembly steps could be completed.

The invention claimed is:

1. A machine for manufacturing personal sanitary items, comprising:
    a first feed mechanism by which a first continuous web of material is directed along a predetermined feed path;
    a pad-making device for preparing a succession of pads for personal sanitary items and applying the single pads to the first web of material;
    a second feed mechanism supplying a second continuous web of material such that the second web can be paired with the first web to produce a succession of sanitary items;
    an accessory mechanism for preparing and applying discrete accessory elements to the personal sanitary items;
    the pad-making device comprising at least one cutter mechanism by which a continuous band of absorbent material is divided up to produce the succession of pads;
    the feed path including a portion describing a trajectory substantially of "S" configuration wherein the first web is directed around a first arc of a first roller, and then around a second arc of a second roller paired with the first roller; the second web being directed around a third arc of the second roller and then the second arc of the second roller, the first roller and the second roller being positioned adjacent to one another to combine the first web and the second web together at a position of tangency between the first roller and the second roller;
    the accessory mechanism positioned at at least one chosen from adjacent to the first roller along the first arc to supply accessory elements to the first web along the first arc and adjacent to the second roller along the third arc to supply accessory elements to the second web along the third.

2. The machine as in claim 1, wherein the first roller and the second roller turn on respective axes of rotation positioned at different heights to one another.

3. The machine as in claim 2, wherein the axis of rotation of the first roller is positioned at a level higher than the axis of rotation of the second roller.

4. The machine as in claim 3, wherein at least one chosen from the first roller and the second roller includes a rubber-coated operating surface.

5. The machine as in claim 1, wherein at least one chosen from the first roller and the second roller is a vacuum roller.

6. The machine as in claim 1, wherein the pad-making device is associated with the first roller.

7. The machine as in claim 1, wherein the second feed mechanism is associated with the second roller.

8. The machine as in claim 1, comprising a dispenser of adhesive positioned upstream of the first roller, by which adhesive is applied at least to the first continuous web of material.

9. The machine as in claim 1, wherein the first roller and the second roller rotate in opposite directions.

10. The machine as in claim 1, wherein at least one chosen from the first roller and the second roller includes a rubber-coated operating surface.

11. The machine as in claim 2, wherein at least one chosen from the first roller and the second roller includes a rubber-coated operating surface.

12. The machine as in claim 1, wherein the accessory mechanism is positioned adjacent to both the first roller along the first arc to supply accessory elements to the first web along the first arc and to the second roller along the third arc to supply accessory elements to the second web along the third arc.

* * * * *